United States Patent
Chang et al.

(10) Patent No.: US 8,545,905 B2
(45) Date of Patent: Oct. 1, 2013

(54) WHITENING COSMETIC COMPOSITION CONTAINING GREEN TEA EXTRACT

(75) Inventors: Hui Kyoung Chang, Yongin-si (KR); Hyang Tee Choi, Yongin-si (KR); Yong Jin Kim, Yongin-si (KR); Seokyun Baek, Yongin-si (KR); Se Jin Yoo, Yongin-si (KR); Jun Cheol Cho, Yongi-si (KR)

(73) Assignee: Amorepacific Corporation, Seoul (KR)

( * ) Notice: Subject to any disclaimer, the term of this patent is extended or adjusted under 35 U.S.C. 154(b) by 28 days.

(21) Appl. No.: 13/280,633

(22) Filed: Oct. 25, 2011

(65) Prior Publication Data

US 2012/0100087 A1  Apr. 26, 2012

(30) Foreign Application Priority Data

Oct. 25, 2010 (KR) .......................... 10-2010-0103932

(51) Int. Cl.
- *A61K 36/00* (2006.01)
- *A61K 8/00* (2006.01)
- *A61K 36/82* (2006.01)

(52) U.S. Cl.
USPC .............................. 424/729; 424/725; 424/62

(58) Field of Classification Search
None
See application file for complete search history.

(56) References Cited

U.S. PATENT DOCUMENTS

2007/0059424 A1 * 3/2007 Iwasaki et al. ................ 426/597

FOREIGN PATENT DOCUMENTS

| JP | 2006271219 A | * | 10/2006 |
| JP | 2008212136 A | * | 9/2008 |

OTHER PUBLICATIONS

English language translation of paragraphs [0031]-[0034] of Takeda (JP 2006027129A).
English language translation paragraphs [0036]-[0039] of Sonoda (JP20080212136A).

* cited by examiner

*Primary Examiner* — Qiuwen Mi
(74) *Attorney, Agent, or Firm* — Nixon & Vanderhye P.C.

(57) ABSTRACT

The present invention relates to a whitening cosmetic composition containing a green tea extract and, more particularly, to a whitening cosmetic composition containing a green tea extract that is prepared from green tea leaves by hot water extraction and liquid culture with *Aspergillus oryzae* to provide a high inhibitory effect on tyrosinase.

2 Claims, 3 Drawing Sheets

WHITENING COSMETIC COMPOSITION CONTAINING GREEN TEA EXTRACT

BACKGROUND OF THE INVENTION

1. Field of the Invention

The present invention relates to a whitening cosmetic composition containing a green tea extract and, more particularly, to a whitening cosmetic composition containing a green tea extract that is prepared from green tea leaves by hot water extraction and then liquid culture with *Aspergillus oryzae* to provide a high inhibitory effect on tyrosinase.

2. Background Art

Human skin color (complexion) is ascribed to various factors, including the activity of melanin-producing melanocytes, the blood vessel distribution, the skin thickness, and the existence of body pigments such as carotenoids, bilirubin, etc. Among these factors, the primary determinant of skin color is a darkening pigment called melanin, which is produced by the actions of different enzymes such as tyrosinase, etc. in the melanocytes. There are three main factors that affect melanin production: genetic factors, physiological factors related to hormone secretions, stress, etc., and environmental factors such as ultraviolet (UV) irradiation. Melanin in humane skin plays an important protective role within the human body against UV light, but overproduction of melanin is known to show up as brown patches and spots on the skin and accelerate skin ageing, even causing skin cancer.

To treat or alleviate skin pigmentation, such as brown spots or patches, and excessive melanin pigmentation caused by UV exposure, cosmetics or medical products have been formulated in combination with ascorbic acid, kojic acid, arbutin, hydroquinone, glutathione, or their derivatives, and tyrosinase-inhibitory substances. However, those substances are restrained in their use due to insufficient whitening effect, skin-safety problems, problems with formulation and safety in cosmetic use, and so forth.

SUMMARY OF THE INVENTION

Through repetitive studies on the substances having an effective inhibitory effect on tyrosinase, the inventors of the present invention have found out that the green tea extract prepared from green tea leaves by hot water extraction and liquid culture with *Aspergillus oryzae* has a high inhibitory effect on tyrosinase, completing the present invention.

It is therefore an object of the present invention to provide a whitening cosmetic composition containing a green tea extract that has an excellent inhibitory effect on tyrosinase.

To accomplish the above object, the present invention provides a whitening cosmetic composition containing a green tea extract fermented with *Aspergillus oryzae*.

Advantageous Effects

The green tea extract of the present invention, which is prepared from green tea leaves by hot water extraction and liquid culture with *Aspergillus oryzae*, is effective in inhibiting the activity of tyrosinase crucial to the production of melanin cells, thereby providing an excellent whitening effect.

DETAILED DESCRIPTION OF THE PREFERRED EMBODIMENT

The present invention relates to a whitening cosmetic composition containing a green tea extract fermented with *Aspergillus oryzae*.

Hereinafter, the present invention will be described in further detail.

The green tea extract used in the present invention may be prepared by a method including the following steps:
(1) subjecting green tea leaves to hot water extraction; (2) cooling the hot water extract by passive cooling; and (3) fermenting the cooled extract with *Aspergillus oryzae*.

Figure 1:
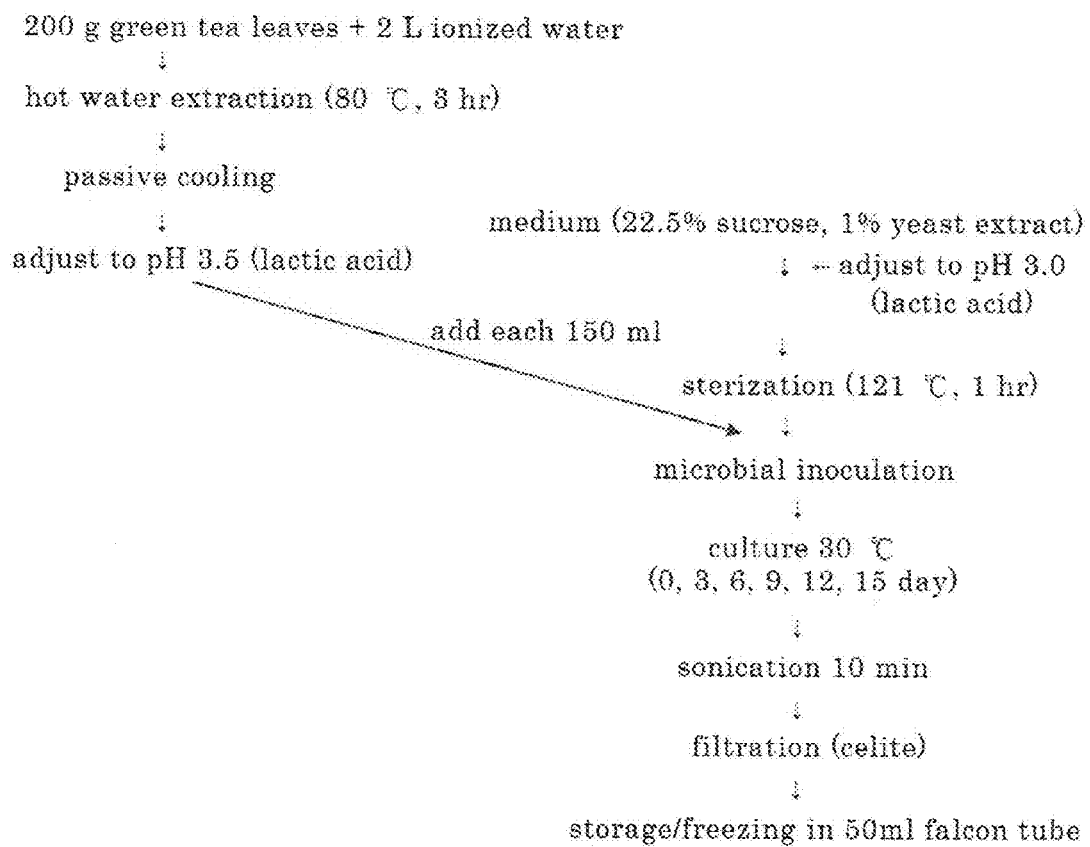
FIG. 1 is a diagram showing a process of preparing a green tea extract by a liquid hot water extraction method using *Aspergillus oryzae* according to the present invention.

The liquid hot water extraction method using *Aspergillus oryzae* in the step (1) is depicted in FIG. 1.

The hot water extraction in the step (1) is preferably carried out at 60 to 90° C., most preferably at 80°. The extraction temperature below 60° C. deteriorates the efficiency of extraction, and the extraction temperature exceeding 90° C. makes the extract unstable.

In the step (3), as for the *Aspergillus oryzae* used, the viable count is $10^5$ to $10^7$ organisms per gram in a batch, and less than $10^6$ in the final product. Undesirably, the viable count less than $10^5$ in the batch of *Aspergillus oryzae* leads to a failure in fermentation, and the viable count exceeding $10^7$ causes contamination with other undesired microorganisms.

Compared with the conventional green tea extracts, the green tea extract of the present invention prepared from green tea leaves by hot water extraction and liquid culture with *Aspergillus oryzae* exhibits a higher inhibitory effect on the activity of tyrosinase to provide a good whitening effect.

The present invention provides a whitening cosmetic composition containing the above-prepared green tea extract. The whitening cosmetic composition contains, based on the total weight of the composition, 0.1 to 40 wt. % of the green tea extract, which is prepared as an effective ingredient from green tea leaves by hot water extraction and liquid culture with *Aspergillus oryzae*. If the content of the green tea extract in the composition is less than 0.1 wt %, whitening effect will not be shown, and if it is more than 40 wt %, an increase in the content thereof will not lead to a further increase in the effect thereof.

The formulation of the cosmetic composition of the present invention includes, but not specifically limited to, toner, facial cream, massage cream, essence, mask, gel, powder, lipstick, foundation make-up, foundation, lotion, ointment, patch, skin solution, foaming cleanser, cleansing cream, cleansing water, soap, spray, etc.

Hereinafter, the present invention will be described in further detail with reference to examples and experimental examples, which are not intended to limit the scope of the present invention.

REFERENCE EXAMPLE 1

Preparation of Fermented Green Tea Leaves

Green tea extracts were fermented with microorganisms, such as yeast (*Saccharomyces cerevisiae*), B. subtilis (*Bacil-* lus subtilis), lactic acid bacteria (*Lactobacillus delbrueckii* spp. *Bulgaricus*), or *Aspergillus oryzae*.

200 g of green tea leaves were soaked in 2 L of an ionized water, subjected to hot water extraction at 80° C. for 3 hours and then passive cooling, and adjusted to pH 3.5 with lactic acid. The liquid hot water extract was cultured with each microorganism.

The microorganism-based culture conditions in a shaking incubator were given as follows. Saccharomyces cerevisiae was cultured in a culture medium containing 0.4% potato starch and 2% dextrose at 25° C. for 72 hours; *Bacillus subtilis* in a culture medium containing 2% dextrose, 0.5% peptone and 0.2% beef extract at 35° C. for 48 hours; *Lactobacillus delbrueckii* spp. *Bulgaricus* in a culture medium containing 2% dextrose, 1% peptone, 1% beef extract and 0.5% yeast extract at 30° C. for 48 hours; *Aspergillus oryzae* in a culture medium containing 5% sucrose and 0.75% yeast extract at 30 for 96 hours.

Each cultured microorganism was collected and isolated from the medium with a primary centrifugal separator. The microorganism isolated was washed with a 0.8 to 1.0% saline solution two to four times, mixed with 0.05 to 22.0% sugar and 0.005 to 10.0% fructose, and then put in a fermented solution, which was sterilized at a high temperature of 120° C. under pressure for 15 minutes and cooled down to a temperature range from the room temperature to 25° C.

EXPERIMENTAL EXAMPLE 1

Inhibitory Effect on Activity Of Tyrosinase Depending on Fermentative Microorganism The inhibitory effect of each fermented green tea extract on the activity of tyrosinase was measured using a method proposed by Vanni et al. (A. Vanni, *Annali Di Chemica*, 80, p35, 1990). More specifically, 1.0 ml of a 0.1M potassium phosphate buffer solution (pH 6.8), 1.0 ml of 0.3 mg/ml an aqueous solution of tyrosine, and 0.1 ml of tyrosinase (1,250 units/ml) were mixed together to prepare a solution. 0.2 ml of the solution by concentration was added to cause an enzymatic reaction at 37° C. for 10 minutes. The absorbance of the reactant solution was measured at 480 nm. The measurement results are presented in FIG. 2.

Figure 2:
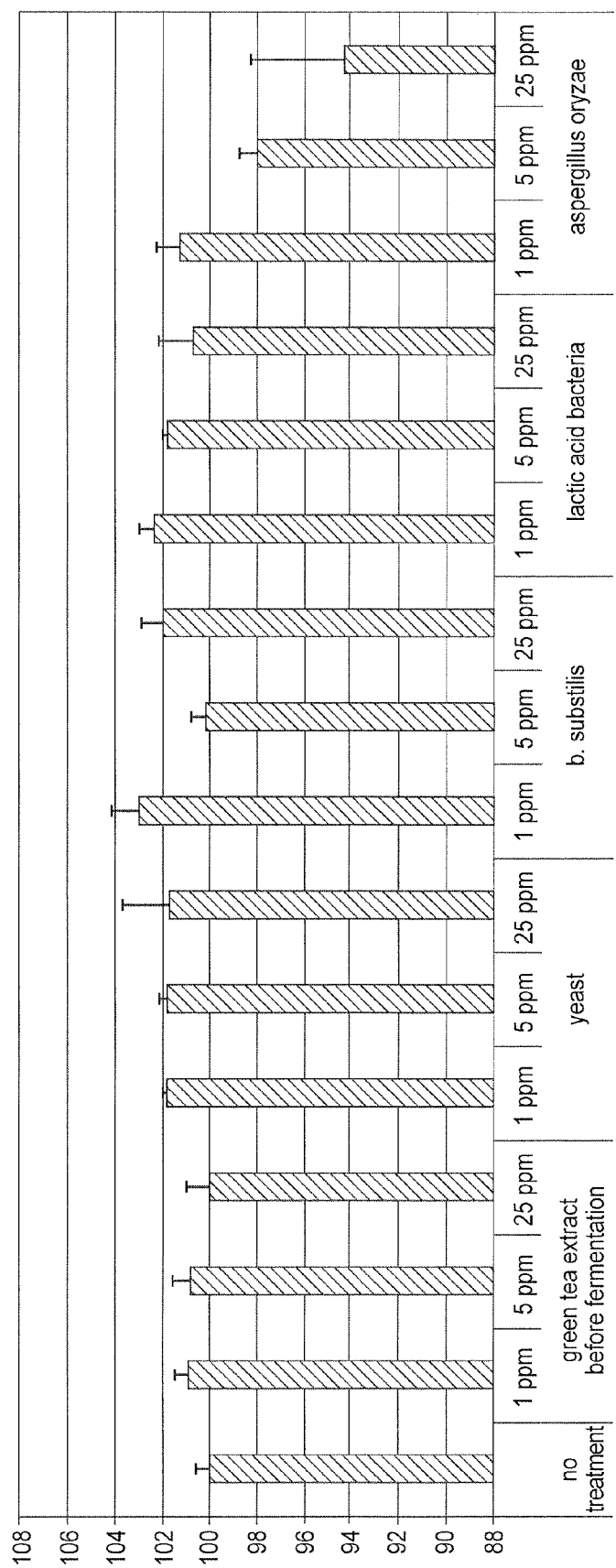
FIG. 2 is a graph showing the inhibitory effect on the activity of tyrosinase depending on the type of microorganism.

As can be seen from FIG. 2, the green teas extracts fermented with yeast, B. subtilis (*Bacillus subtilis*), and lactic acid bacteria had no inhibitory effect on tyrosinase as the green tea extract before fermentation, while the green tea extract treated with 25 ppm of *Aspergillus oryzae* inhibited the activity of tyrosinase.

EXAMPLE 1

Preparation of Liquid Hot Water Extract Using *Aspergillus Oryzae*

200 g of green tea leaves were soaked in 2 L of ionized water, subjected to hot water extraction at 80° C. for 3 hours and then passive cooling, and adjusted to pH 3.5 with lactic acid. Apart from this, a culture medium containing 22.5% sucrose and 1% yeast extract was adjusted to pH 3.0 with lactic acid, and then sterilized at 121° C. for 1 hour. To the culture medium was added each 150 mL of the liquid hot water extract and inoculated *Aspergillus oryzae* to cause fermentation at 30° C. The fermented solution thus obtained was subjected to sonication for 10 minutes, filtered with celite and stored/frozen in a 50 mL-Falcon tube to prepare a liquid hot water extract using *Aspergillus oryzae*.

COMPARATIVE EXAMPLE 1

Preparation of Solid Alcohol Extract Using *Aspergillus Oryzae*

200 g of green tea leaves were soaked in 2 L of 70% ethanol and subjected to hot water extraction at the room temperature for 3 hours and then freeze drying. Apart from this, a culture medium containing 22.5% sucrose and 1% yeast extract was adjusted to pH 3.0 with lactic acid, and sterilized at 121° C. for 1 hour. To the culture medium was added each 10 g of the solid alcohol extract and inoculated *Aspergillus oryzae* to cause fermentation at 30° C. The fermented solution thus obtained was subjected to sonication for 10 minutes, filtered with celite and stored/frozen in a 50 mL-Falcon tube to prepare a solid alcohol extract using *Aspergillus oryzae*.

COMPARATIVE EXAMPLE 2

Preparation of Solid Hot Water Extract Using *Aspergillus Oryzae*

200 g of green tea leaves were soaked in 2 L of ionized water, subjected to hot water extraction at 80° C. for 3 hours and then freeze drying. Apart from this, a culture medium containing 22.5% sucrose and 1% yeast extract was adjusted to pH 3.0 with lactic acid, and sterilized at 121° C. for 1 hour. To the culture medium was added 10 g of the solid hot water extract and inoculated *Aspergillus oryzae* to cause fermentation at 30° C. The fermented solution thus obtained was subjected to sonication for 10 minutes, filtered with celite and stored/frozen in a 50 mL-Falcon tube to prepare a solid hot water extract using *Aspergillus oryzae*.

COMPARATIVE EXAMPLE 3

Preparation of Liquid Alcohol Extract Using *Aspergillus Oryzae*

200 g of green tea leaves were soaked in 2 L of 70% ethanol, subjected to alcohol extraction at the room temperature for 3 hours and then passive cooling, and adjusted to pH 3.5 with lactic acid. Apart from this, a culture medium containing 22.5% sucrose and 1% yeast extract was adjusted to pH 3.0 with lactic acid and sterilized at 121° C. for 1 hour. To the culture medium was added each 150 mL of the liquid alcohol extract and inoculated *Aspergillus oryzae* to cause fermentation at 30° C. The fermented solution thus obtained was subjected to sonication for 10 minutes, filtered with celite and stored/frozen in a 50 mL-Falcon tube to prepare a liquid alcohol extract using *Aspergillus oryzae*.

COMPARATIVE EXAMPLE 4

Preparation of Green Tea Extract Before Fermentation 200 g of dry green tea leaves were soaked in 2 L of 70% ethanol, subjected to three times of reflux extraction and then settled at 15° C. for one day. Subsequently, filtration with a filter cloth and centrifugal separation were performed to achieve separation into residue and filtrate. The filtrate thus obtained was then concentrated under reduced pressure to prepare a green tea extract before fermentation.

EXPERIMENTAL EXAMPLE 2

Inhibitory Effect on Activity of Tyrosinase Depending on Conditions for Fermentation with *Aspergillus Oryzae* and Extraction of Green Tea Leaves Using the Example 1 and the Comparative Examples 1 to 4, the procedures were performed in the same manner as described in the Experimental Example 1 to evaluate the respective samples in regard to the inhibitory effect on the activity of tyrosinase. The results are presented in FIG. 3.

Figure 3:
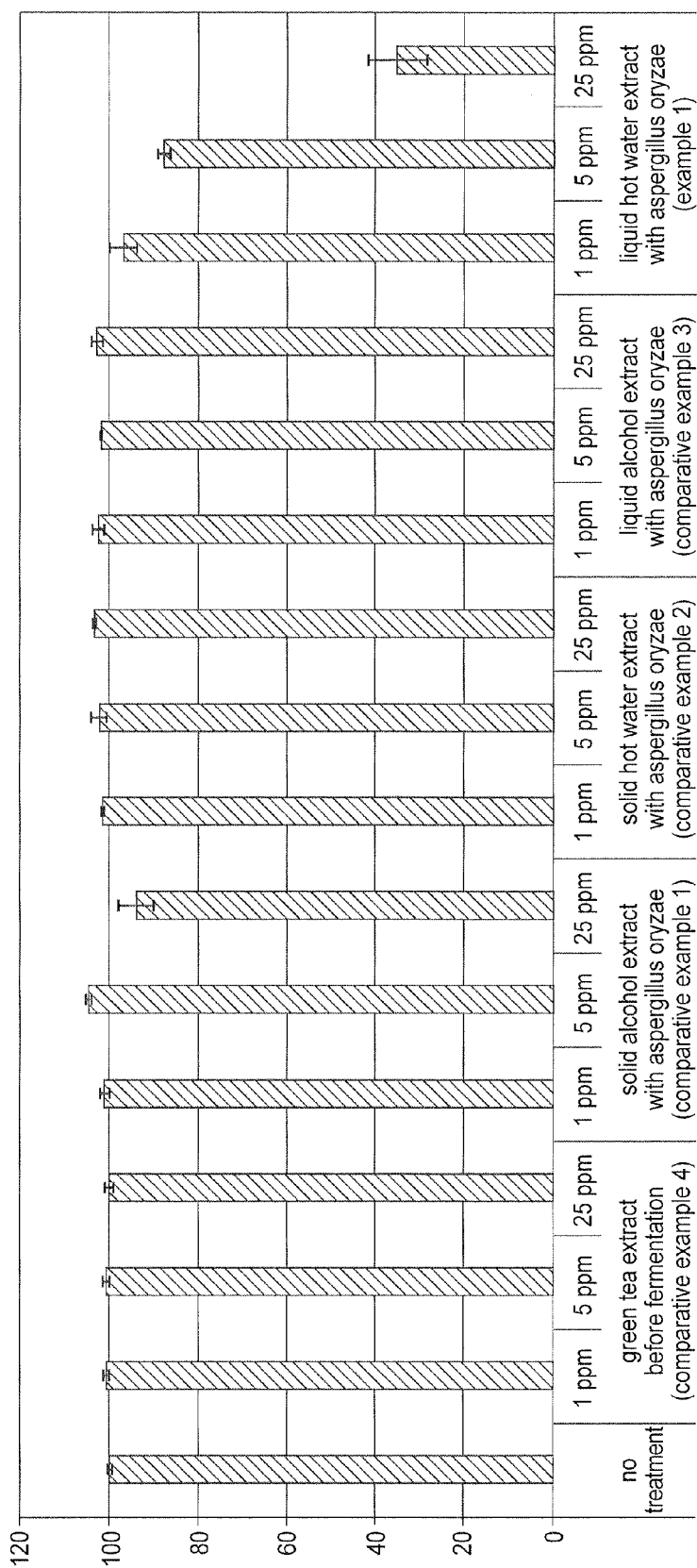
FIG. 3 is a graph showing the inhibitory effect on the activity of tyrosinase depending on green tea extraction conditions and fermentation conditions using *Aspergillus oryzae*.

As can be seen from FIG. 3, the green tea extract prepared by fermenting a hot water extract of green tea leaves with *Aspergillus oryzae* through liquid culture fermentation had a good inhibitory effect on the activity of tyrosinase in proportion to its concentration. On the contrary, there was little inhibitory effect on the activity of tyrosinase in the green tea extracts in the Comparative Examples 1, 2 and 3 using solid alcohol extraction, solid hot water extraction, or liquid alcohol extraction, and in the Comparative Example 4 using no fermentation process.

FORMULATION EXAMPLE 1

Preparation of Toner (Emulsion)

TABLE 1

| Ingredient | Content (wt. %) |
| --- | --- |
| Purified Water | Remainder |
| Glycerin | 8.0 |
| Butylene Glycol | 4.0 |
| Hyaluronic Acid | 5.0 |
| β-Glucan | 7.0 |
| Carbomer | 0.1 |
| Green Tea Extract Using *Aspergillus Oryzae* | 2.0 |
| Caprylic/Capric Triglyceride | 8.0 |
| Squalene | 5.0 |
| Cetearyl Glucoside | 1.5 |
| Sorbitan Stearate | 0.4 |
| Cetearyl Alcohol | 1.0 |
| Preservative, Flavor, Color | Proper Amount |
| Triethanol Amine | 0.1 |

FORMULATION EXAMPLE 2

Preparation of Facial Cream

TABLE 2

| Ingredient | Content (wt. %) |
| --- | --- |
| Purified Water | Remainder |
| Glycerin | 3.0 |
| Butylene Glycol | 3.0 |
| Paraffin Oil | 7.0 |
| β-Glucan | 7.0 |
| Carbomer | 0.1 |
| Green Tea Extract Using *Aspergillus Oryzae* | 2.0 |

TABLE 2-continued

| Ingredient | Content (wt. %) |
| --- | --- |
| Caprylic/Capric Triglyceride | 3.0 |
| Squalene | 5.0 |
| Cetearyl Glucoside | 1.5 |
| Sorbitan Stearate | 0.4 |
| Polysorbate | 1.2 |
| Preservative, Flavor, Color | Proper Amount |
| Triethanol Amine | 0.1 |

FORMULATION EXAMPLE 3

Preparation of Massage Cream

TABLE 3

| Ingredient | Content (wt. %) |
| --- | --- |
| Purified Water | Remainder |
| Glycerin | 8.0 |
| Butylene Glycol | 4.0 |
| Paraffin Oil | 45.0 |
| β-Glucan | 7.0 |
| Carbomer | 0.1 |
| Green Tea Extract Using *Aspergillus Oryzae* | 2.0 |
| Caprylic/Capric Triglyceride | 3.0 |
| Wax | 4.0 |
| Cetearyl Glucoside | 1.5 |
| Sorbitan Sesquioleate | 0.9 |
| Vaseline | 3.0 |
| Preservative, Flavor, Color | Proper Amount |
| Triethanol Amine | 0.1 |

FORMULATION EXAMPLE 4

Preparation of Ointment

TABLE 4

| Ingredient | Content (wt. %) |
| --- | --- |
| Purified Water | Remainder |
| Glycerin | 8.0 |
| Butylene Glycol | 4.0 |
| Paraffin Oil | 15.0 |
| β-Glucan | 7.0 |
| Carbomer | 0.1 |
| Green Tea Extract Using *Aspergillus Oryzae* | 2.0 |
| Caprylic/Capric Triglyceride | 3.0 |
| Squalene | 1.0 |
| Cetearyl Glucoside | 1.5 |
| Sorbitan Stearate | 0.4 |
| Cetearyl Alcohol | 1.0 |
| Preservative, Flavor, Color | Proper Amount |
| Wax | 4.0 |

What is claimed is:

1. A method of whitening the skin, comprising topically administering a composition comprising a green tea extract fermented with 25 ppm of *Aspergillus oryzae*.

2. A method of inhibiting tyrosinase, comprising topically administering a composition comprising a green tea extract fermented with 25 ppm of *Aspergillus oryzae*.

* * * * *